(12) United States Patent
Wang et al.

(10) Patent No.: US 9,855,705 B2
(45) Date of Patent: Jan. 2, 2018

(54) METHOD OF INCREASING STENT RETENTION OF BIOABSORBABLE SCAFFOLDING WITH A SHEATH

(71) Applicant: Abbott Cardiovascular Systems Inc., Santa Clara, CA (US)

(72) Inventors: Yunbing Wang, Sunnyvale, CA (US); Xiao Ma, Santa Clara, CA (US); Rommel Lumauig, San Jose, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 304 days.

(21) Appl. No.: 14/692,615

(22) Filed: Apr. 21, 2015

(65) Prior Publication Data

US 2015/0224707 A1   Aug. 13, 2015

Related U.S. Application Data

(62) Division of application No. 13/103,882, filed on May 9, 2011, now abandoned.

(51) Int. Cl.
| | |
|---|---|
| *B29C 65/56* | (2006.01) |
| *A61F 2/958* | (2013.01) |
| *A61F 2/915* | (2013.01) |
| *A61F 2/95* | (2013.01) |

(52) U.S. Cl.
CPC .......... *B29C 65/567* (2013.01); *A61F 2/958* (2013.01); *A61F 2/915* (2013.01); *A61F 2002/9522* (2013.01); *Y10T 29/49925* (2015.01)

(58) Field of Classification Search
None
See application file for complete search history.

(56) References Cited

U.S. PATENT DOCUMENTS

| | | | |
|---|---|---|---|
| 5,836,965 A | 11/1998 | Jendersee et al. |
| 5,893,868 A | 4/1999 | Hanson et al. |
| 5,913,871 A | 6/1999 | Werneth et al. |
| 5,976,181 A | 11/1999 | Whelan et al. |
| 6,063,092 A | 5/2000 | Shin |
| 6,159,237 A | 12/2000 | Alt et al. |
| 6,629,350 B2 | 10/2003 | Motsenbocker |
| 6,666,880 B1 | 12/2003 | Chiu et al. |
| 6,682,553 B1 | 1/2004 | Webler, Jr. |

(Continued)

FOREIGN PATENT DOCUMENTS

| | | |
|---|---|---|
| EP | 0 787 020 | 5/1996 |
| EP | 1 226 798 | 5/2000 |

(Continued)

*Primary Examiner* — Monica Huson
(74) *Attorney, Agent, or Firm* — Squire Patton Boggs (US) LLP

(57) ABSTRACT

A medical device includes a polymer stent crimped to a catheter having an expansion balloon. The stent is crimped to the balloon by a process that includes heating the stent to a temperature below the polymer's glass transition temperature to improve stent retention without adversely affecting the mechanical characteristics of the stent when later deployed to support a body lumen. A variable diameter sheath with a central portion that prevents expansion of the stent when the balloon is pressurized and larger diameter ends is disposed over the crimped stent-balloon assembly. The balloon is pressurized and the larger diameter ends of the sheath allow the balloon beyond the ends of the stent to expand. The balloon is then depressurized.

19 Claims, 7 Drawing Sheets

(56) References Cited

U.S. PATENT DOCUMENTS

| | | |
|---|---|---|
| 6,745,445 B2 | 6/2004 | Spilka |
| 6,863,683 B2 | 3/2005 | Schwager et al. |
| 6,948,223 B2 | 9/2005 | Shortt |
| 7,010,850 B2 | 3/2006 | Hijlkema et al. |
| 7,316,148 B2 | 1/2008 | Asmus et al. |
| 7,666,342 B2 | 2/2010 | Limon et al. |
| 7,761,968 B2 | 7/2010 | Huang et al. |
| 7,951,185 B1 | 5/2011 | Abbate et al. |
| 8,002,817 B2 | 8/2011 | Limon |
| 8,012,402 B2 | 9/2011 | Kleiner et al. |
| 8,123,793 B2 | 2/2012 | Roach et al. |
| 8,261,423 B2 | 9/2012 | Jow et al. |
| 8,318,078 B2 | 11/2012 | Jagger et al. |
| 2002/0143382 A1 | 10/2002 | Hijlkema et al. |
| 2004/0078953 A1 | 4/2004 | Spilka |
| 2004/0106973 A1 | 6/2004 | Johnson |
| 2004/0138731 A1 | 7/2004 | Johnson |
| 2005/0119720 A1 | 6/2005 | Gale et al. |
| 2005/0143752 A1 | 6/2005 | Schwager et al. |
| 2006/0009832 A1 | 1/2006 | Fisher |
| 2006/0047336 A1 | 3/2006 | Gale et al. |
| 2007/0006441 A1 | 1/2007 | McNiven et al. |
| 2007/0204455 A1 | 9/2007 | Knott et al. |
| 2007/0271763 A1 | 11/2007 | Huang et al. |
| 2007/0282433 A1 | 12/2007 | Limon et al. |
| 2007/0289117 A1 | 12/2007 | Huang et al. |
| 2008/0016668 A1 | 1/2008 | Huang et al. |
| 2008/0033523 A1 | 2/2008 | Gale et al. |
| 2008/0033524 A1 | 2/2008 | Gale |
| 2008/0147164 A1 | 6/2008 | Gale et al. |
| 2008/0275537 A1 | 11/2008 | Limon |
| 2009/0001633 A1 | 1/2009 | Limon et al. |
| 2009/0088829 A1 | 4/2009 | Wang et al. |
| 2009/0105800 A1 | 4/2009 | Sabaria |
| 2010/0004735 A1 | 1/2010 | Yang et al. |
| 2010/0025894 A1 | 2/2010 | Kleiner et al. |
| 2010/0063571 A1 | 3/2010 | Roach et al. |
| 2010/0323091 A1 | 12/2010 | Castro et al. |
| 2011/0270383 A1 | 11/2011 | Jow et al. |
| 2011/0271513 A1 | 11/2011 | Wang |
| 2012/0010693 A1 | 1/2012 | Van Sciver |
| 2012/0042501 A1 | 2/2012 | Wang et al. |
| 2012/0079706 A1 | 4/2012 | Knott et al. |

FOREIGN PATENT DOCUMENTS

| | | |
|---|---|---|
| EP | 1 295 570 | 7/2002 |
| EP | 2 029 052 | 3/2003 |
| WO | WO 99/55406 | 11/1999 |
| WO | WO 02/102283 | 12/2002 |
| WO | WO 2005/053937 | 6/2005 |
| WO | WO 2006110861 | 10/2006 |
| WO | WO 2007/146354 | 12/2007 |
| WO | WO 2008/033621 | 3/2008 |
| WO | WO 2010/151497 | 12/2010 |

METHOD OF INCREASING STENT RETENTION OF BIOABSORBABLE SCAFFOLDING WITH A SHEATH

This application is a divisional application of U.S. application Ser. No. 13/103,882, filed on May 9, 2011.

BACKGROUND OF THE INVENTION

Field of the Invention

The present invention relates to medical devices; more particularly, this invention relates to methods of making polymeric stent delivery systems.

Background of the Invention

The art recognizes a variety of factors that affect a polymeric stent's ability to retain its structural integrity when subjected to external loadings, such as crimping and balloon expansion forces. These interactions are complex and the mechanisms of action not fully understood. According to the art, characteristics differentiating a polymeric, bio-absorbable stent scaffolding of the type expanded to a deployed state by plastic deformation from a similarly functioning metal stent are many and significant. Indeed, several of the accepted analytic or empirical methods/models used to predict the behavior of metallic stents tend to be unreliable, if not inappropriate, as methods/models for reliably and consistently predicting the highly non-linear behavior of a polymeric load-bearing, or scaffolding portion of a balloon-expandable stent. The models are not generally capable of providing an acceptable degree of certainty required for purposes of implanting the stent within a body, or predicting/anticipating the empirical data.

Moreover, it is recognized that the state of the art in medical device-related balloon fabrication, e.g., non-compliant balloons for stent deployment and/or angioplasty, provide only limited information about how a polymeric material might behave when used to support a lumen within a living being via plastic deformation of a network of rings interconnected by struts. In short, methods devised to improve mechanical features of an inflated, thin-walled balloon structure, most analogous to mechanical properties of a pre-loaded membrane when the balloon is inflated and supporting a lumen, simply provides little, if any insight into the behavior of a deployed polymeric stent scaffolding. One difference, for example, is the propensity for fracture or cracks to develop in a stent scaffolding. The art recognizes the mechanical problem as too different to provide helpful insights, therefore, despite a shared similarity in class of material. At best, the balloon fabrication art provides only general guidance for one seeking to improve characteristics of a balloon-expanded, bio-absorbable polymeric stent.

Polymer material considered for use as a polymeric stent scaffolding, e.g. PLLA or PLGA, may be described, through comparison with a metallic material used to form a stent scaffolding, in some of the following ways. A suitable polymer has a low strength to weight ratio, which means more material is needed to provide an equivalent mechanical property to that of a metal. Therefore, struts must be made thicker and wider to have the strength needed to support a lumen, for example. The scaffolding also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly, bio-absorbable polymer such as PLLA or PLGA.

Processing steps performed on, design changes made to a metal stent that have not typically raised concerns for, or require careful attention to unanticipated changes in the average mechanical properties of the material, therefore, may not also apply to a polymer stent due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after stent fabrication, e.g., crimping. As a consequence, a change to a fabrication process, post-fabrication process, diameter of the stent, length of the stent, or even relatively minor changes to a stent pattern design must, generally speaking, be investigated more thoroughly than if a metallic material were used instead of the polymer. It follows, therefore, that when choosing among different polymeric stent designs for improvement thereof, there are far less inferences, theories, or systematic methods of discovery available, as a tool for steering one clear of unproductive paths, and towards more productive paths for improvement, than when making changes in a metal stent.

It is recognized, therefore, that, whereas inferences previously accepted in the art for stent validation or feasibility when an isotropic and ductile metallic material was used, such inferences would be inappropriate for a polymeric stent. A change in a polymeric stent pattern may affect not only the stiffness or lumen coverage of the stent in its deployed state supporting a lumen, but also the propensity for fractures to develop when the stent is crimped or being deployed. This means that, in comparison to a metallic stent, there is generally no assumption that can be made as to whether a changed stent pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the geometry of the stent such as length, diameter, strut thickness, and pattern of the struts and rings of a polymeric stent scaffolding that is plastically deformed, both when crimped to, and when later deployed by a balloon, unfortunately, is not as easy to predict as a metal stent. Indeed, it is recognized that unexpected problems may arise in polymer stent fabrication steps as a result of a changed pattern that would not have necessitated any changes if the pattern was instead formed from a metal tube. In contrast to changes in a metallic stent pattern, a change in polymer stent pattern may necessitate other modifications in fabrication steps or post-fabrication processing, such as crimping and sterilization.

One problem frequently encountered with a stent for delivery to a site in a body using a balloon is reliably retaining the stent on the balloon as it passes through tortuous anatomy. If the stent is not held on the balloon with sufficient force, it can slip off of the balloon during transit to the target site. For a metallic stent, there are several approaches proposed for increasing the retention of a stent to a balloon during transit to the target site. However, methods proposed thus far for retaining the polymer stent on a balloon are in need of improvement.

In light of the foregoing problems, there is a need for improving the retention of a polymer stent on a balloon while avoiding adverse effects on the mechanical characteristics of the load bearing, polymer scaffolding when the scaffolding is fully deployed to support a lumen.

SUMMARY OF THE INVENTION

Various embodiments of the present invention include a method of making a stent delivery system, comprising the steps of: providing a polymeric scaffolding crimped tightly over a delivery balloon; providing a tubular sheath comprising a middle portion and two end portions, wherein the middle portion of the sheath have an inside diameter equal to or 1-2% larger than the outer diameter of the crimped scaffolding and the end portions of the sheath have a diameter 3-100% greater than the diameter of the crimped scaffolding; disposing the polymeric scaffolding and balloon within the tubular sheath, wherein the middle portion of the sheath is disposed over the scaffolding and the end portions of the sheath extend beyond the ends of the scaffolding over end portions of the balloon; pressurizing the balloon to cause the end portions of the balloon to inflate beyond the outer diameter of the crimped scaffolding; and depressurizing the balloon.

Further embodiments of the present invention include a method of making a stent delivery system, comprising the steps of: providing a polymeric scaffolding; crimping the scaffolding to a final crimped diameter over a balloon to form a crimped stent-balloon assembly, wherein the crimping includes at least one crimping step in which the scaffolding is crimped to a first diameter greater than the final diameter and holding the scaffolding at the first diameter while the balloon is inflated to a pressure against the scaffolding; providing a tubular sheath comprising a central portion; disposing the polymeric stent and balloon within the tubular sheath, wherein the central portion prevents expansion of the stent when the balloon is pressurized; pressurizing the balloon to cause end portions of the balloon proximal and distal to ends of the stent to expand; and depressurizing the balloon.

Additional embodiments of the present invention include a stent delivery system, comprising: a tubular sheath comprising a middle portion and two end portions; a polymeric scaffolding crimped tightly over a delivery balloon, wherein the polymeric scaffolding and balloon are disposed within the tubular sheath; wherein the middle portion of the sheath has an inside diameter equal to or 1-2% larger than the outer diameter of the crimped scaffolding and the end portions of the sheath have a diameter greater than the diameter of the crimped scaffolding; wherein the middle portion of the sheath is disposed over the scaffolding and the end portions of the sheath extend beyond the ends of the scaffolding over end portions of the balloon.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

DETAILED DESCRIPTION OF EMBODIMENTS

Figure 1:
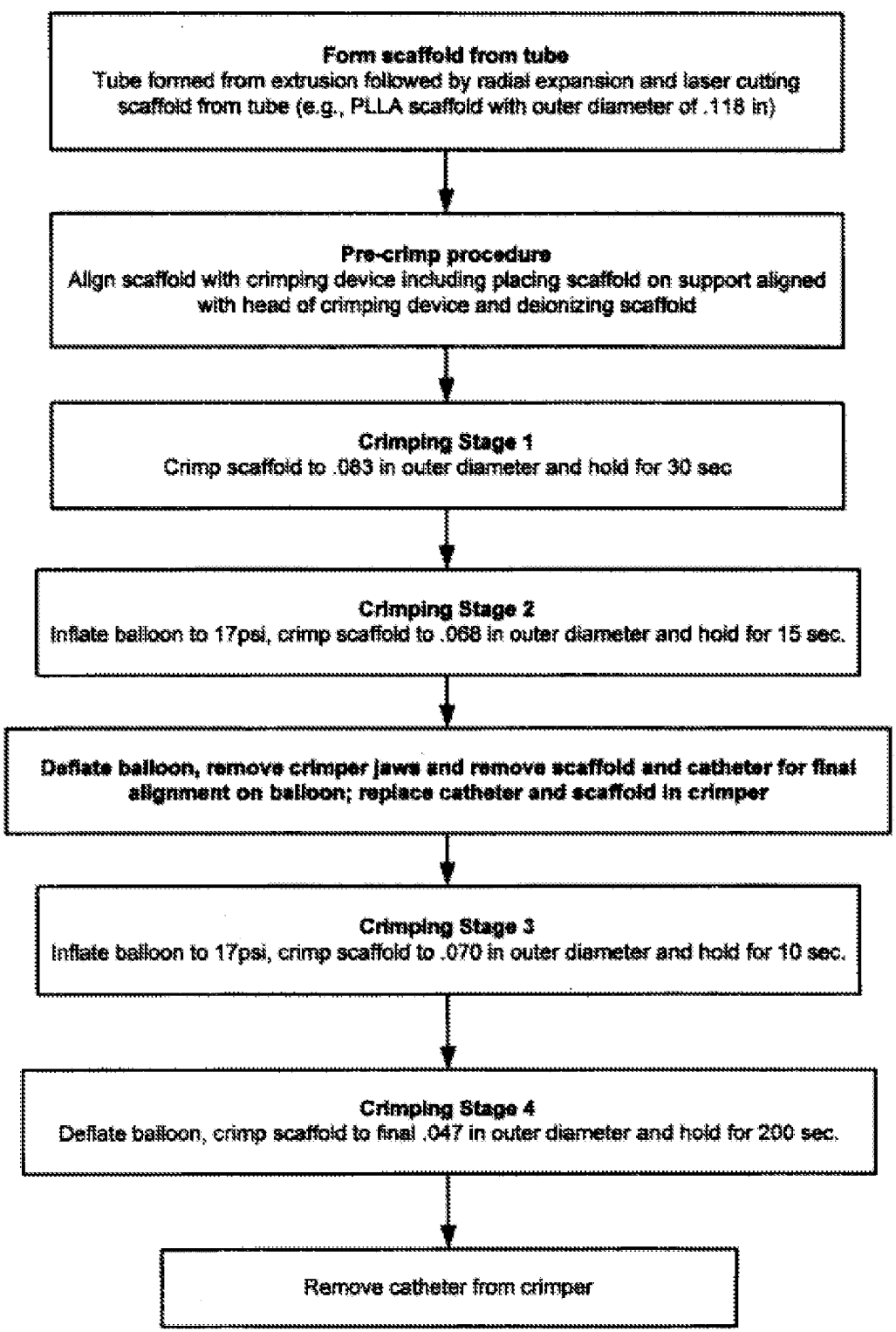
FIG. 1 shows a process for fabricating a scaffolding of a polymer stent and crimping the fabricated stent to a balloon according to the invention.

The "glass transition temperature," Tg, is the temperature at which the amorphous domains of a polymer generally change from a brittle, vitreous state to a solid deformable or ductile state at atmospheric pressure. In other words, the Tg corresponds to the temperature where the onset of noticeable segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

Poly(lactide-co-glycolide) (PLGA) and Poly (L-lactide) (PLLA) are examples of a class of semi-crystalline polymers that may be used to form the scaffolding for the stent structures described herein. PLLA is a homopolymer and PLGA is a co-polymer. The percentage of glycolide (GA) in a scaffold constructed of PLGA may vary, which can influence the lower range of Tg. For example, the percentage of GA in the matrix material may vary between 0-15%. For PLLA, the onset of glass transition occurs at about 55 degrees Celsius. With an increase of GA from about 0% to 15% the lower range for Tg for PLGA can be correspondingly lower by about 5 degrees Celsius.

In one embodiment, a tube is formed by an extrusion of PLLA. The tube forming process described in US Pub. No. 2010/00025894 may be used to form this tube. The finished, solidified polymeric tube of PLLA may then be deformed in radial and axial directions by a blow molding process wherein deformation occurs progressively at a predetermined longitudinal speed along the longitudinal axis of the tube. For example, blow molding can be performed as described in U.S. Publication No. 2009/0001633. This biaxial deformation, after the tube is formed, can produce noticeable improvement in the mechanical properties of the stent structural members cut from the tube without this expansion. The degree of radial expansion that the polymer tube undergoes characterizes the degree of induced circumferential molecular or crystal orientation. In a preferred embodiment, the radial expansion ratio or RE ratio is about 450% of the starting tube's inner diameter and the axial expansion ratio or AE ratio is about 150% of the starting tube's length. The ratios RA and AE are defined in US Pub. No. 2010/00025894.

The above scaffolding's outer diameter may be designated by where it is expected to be used, e.g., a specific location or area in the body. The outer diameter, however, is usually only an approximation of what will be needed during the procedure. For instance, there may be extensive calcification that breaks down once a therapeutic agent takes effect, which can cause the stent to dislodge in the vessel. Further, since a vessel wall cannot be assumed as circular in cross-section, and its actual size only an approximation, a physician can choose to over-extend the stent to ensure it stays in place. For this reason, it is preferred to use a tube with a diameter larger than the expected deployed diameter of the stent.

In one embodiment the ratio of deployed to fully crimped diameter is about 2.5. In this embodiment, the crimped diameter corresponds to an outer diameter that is only about 40% of the starting diameter. Hence, when deployed the drug eluting stent is expected to increase in size up to about 2.5 times its stowed or crimped diameter size.

In one particular example, a stent is formed from a biaxially expanded tube having an outer diameter of 3.5 mm, which approximately corresponds to a deployed diameter (the stent may be safely expanded up to 4.0 mm within a lumen). When crimped on the balloon, the stent has an outer diameter of 1.3 mm, or about 37% of the starting tube diameter of 3.5 mm.

As discussed earlier, fabrication of a balloon-expanded polymer stent presents challenges that are not present in metallic stents. One challenge, in particular, is the fabrication of a polymer scaffolding, which means the load bearing network of struts including connectors linking ring elements or members that provide the radial strength and stiffness needed to support a lumen. In particular, there exists ongoing challenges in fabricating a polymer scaffolding (hereinafter "scaffolding") that is capable of undergoing a significant degree of plastic deformation without loss of strength, e.g., cracks or fracture of struts. In the disclosed embodiments, a polymer scaffolding is capable of being deformed from a crimped diameter to at least 2.5 times the crimped diameter without significant loss of strength. Moreover, the polymer scaffolding is retained on a delivery balloon with a retention force that is significantly higher than previous methods of stent retention for a polymer stent.

One problem encountered with fabrication of a stent for delivery to a site in a body using a balloon is the ability of the stent to be safely crimped to the balloon so that an adequate retention force is established between the stent and balloon. A "retention force" for a stent crimped to a balloon means the maximum dislodgement force, applied to the stent along the direction of travel through a vessel, that the stent-balloon is able to resist before dislodging the stent from the balloon.

The invention addresses the unique challenges presented by a polymer stent that needs to be retained on a balloon. These challenges are present for several reasons. First, there is less space available between struts in a crimped state, which prevents balloon material from extending within gaps between struts. As a result, there is less abutment or interference between struts and balloon material, which interference/abutment has previously been relied upon to increase the retention force of the stent on a balloon. This condition is a result of the need to fabricate wider and thicker struts for the polymer stent, as compared to a metal stent, so as to provide adequate, deployed radial strength.

Second, a polymer, unlike a metal, is far more sensitive to changes in temperature. The art has previously relied on heat to retain a metal stent on a balloon. However, the temperatures that have previously been found effective for stent retention fall within a Tg of the polymer. Such temperature ranges have, therefore, been avoided since heating of a polymer scaffolding to within, or above Tg induces significant changes in the molecular orientation of the polymer material that result in loss of strength when the scaffolding is plastically deformed to its deployed diameter.

The retention force for a stent on a balloon is set by a process of mounting the stent on a balloon which includes a crimping process. In the crimping process the stent is plastically deformed onto the balloon surface to form a fit that resists dislodgment of the stent from the stent. Factors affecting the retention of a stent on a balloon are many. They include the extent of surface-to-surface contact between the balloon and stent, the coefficient of friction of the balloon and stent surfaces, and the degree of protrusion or extension of balloon material between struts of the stent. In general, a preferred range of retention force for a stent is greater than 0.7 lb, 0.7 to 1.2 lb, or greater than 1.2 lb.

For a metal stent there are a wide variety of methods known for improving the retention force of a stent on a balloon via modification of one or more of the foregoing properties; however, many are not suitable or of limited usefulness for a polymeric stent, due to differences in mechanical characteristics of a polymer stent verses a metal stent as discussed earlier. Most notable among these differences is brittleness of the polymer material suitable for balloon-expanded stent fabrication, verses that of a metal stent. Whereas a metal stent may be deformed sufficiently to obtain a desired retention force, the range of deformation available to a polymer stent, while avoiding cracking or fracture-related problems, by comparison, is quite limited.

The art has previously devised methods for retaining a polymer stent on a delivery balloon in response to these challenges. Applicants and others have applied such previously devised methods to crimping polymeric stents. Initial approaches focused on enhancing the contribution to stent retention provided by the stent ends. In one example, the stent is crimped to the delivery balloon at a temperature well below the polymer's Tg, for example, about 30° C., as described in 20050119720. A method originally developed for improving retention of metal stents is then applied to the stent that is tightly crimped onto the balloon as described in U.S. Pat. No. 6,666,880 to Chiu et al. An expansion restraint is placed over the stent and the balloon. The restraint has an inner diameter equal to the outer diameter of the crimped stent. The stent is kept cool by a stent temperature controller and is thermally insulated while a portion of the catheter balloon extending beyond the edge of the stent is heated by a heat source. The balloon is pressurized which causes the balloon at the end of the stent to inflate and conform to the stent's geometry. Specifically, the expanded balloon ends form raised edges abutting the stent ends to resist dislodgment of the stent from the balloon. The expansion restraint prevents the balloon from extending beyond the outer diameter of the stent both in the gaps between struts and at then ends. Preventing balloon material from being pumped out beyond the stent outer surface was thought necessary for metal stents since metal stent have sharp edges that could cause pinholes in the balloon.

The above disclosed method provided a retention force between 0.5 and 0.7 lb. In one example, this process provided a retention force of about 0.35 lb. for a Poly (L-lactide) (PLLA) scaffolding crimped to a polymide-polyether block co-polymer (PEBAX) balloon. Although adequate, improvement in retention force was needed.

A second approach taken to obtaining improved stent retention focused on the interaction of the stent surface with the balloon and stent ends interaction with the balloon. This second approach did not include a step post-crimping that involved preferential inflation of the balloon at the ends of the stent, as described above. This second approach is described in U.S. patent application Ser. No. 12/772,116 to Jow et al. In this method, the crimping head reduces the stent diameter in stages as well as heating the stent. In addition, the balloon is pressurized during some of the stages so that the stent is crimped over an inflated balloon. This method resulted in significant improvement of the retention force of a polymeric stent on a balloon. The method is described in detail below.

During the development the approach of Jow et al., it was found, unexpectedly, that there is a certain degree of beneficial movement between interconnected polymer chains of a stent structure heated to temperatures just below Tg of the polymer when the stent is being crimped to a balloon, versus the same stent crimped to the balloon at a lower temperature, such as room temperature. For example, for a controlled temperature of between about 48 and 54 degrees, 48-50 degrees or 48 degrees Celsius it was found that a PLLA stent crimped to a balloon exhibited noticeable improvement in the retention force of the stent on the balloon, while not concomitantly producing unacceptable side effects for the deployed stent, e.g., excessive cracking or void formation, fracture or loss of memory in the material affecting its deployed radial stiffness qualities. The temperature range can also be 45 to 55 degrees Celsius.

A solution for improvement of the retention provided by Jow et al. was found from a series of studies involving increasing or varying balloon pressure during crimping, initiating stages of stent crimping including different rates, interim and final hold times at various crimper diameters, e.g., pre-crimping steps, or increasing the temperature of the stent while it was being crimped, or a combination of these factors. A preliminary study was conducted to determine whether modification of one or more of these factors in a polymer scaffold crimping process might improve stent retention. Thus, factors including temperature, hold time, balloon pressure force, pressure sequence, pressure initiation size, and speed of crimping were initially studied and results collected and studying under a multi-factored statistical approach to identify the key factors altering scaffold retention to a balloon. For this preliminary study, an iris crimper was used to crimp the stent. The scaffold was heated by heating the crimper jaws, although the scaffold may alternatively be heated by a forced hot air gas or heated fluid for expanding the balloon.

Based on this multi-factored study it was hypothesized that a carefully chosen temperature range might improve results, which came as a surprise. It was previously believed there would be little, or no benefit to heating a scaffold during crimping because either a raised temperature would induce molecular motion destroying the chain alignment needed to give the scaffold its deployed strength properties, or the temperature was too low to affect either the scaffold or the balloon.

A more narrow-focused study was conducted to identify a temperature range that might produce a significant difference in scaffold retention force without causing adverse effects on the deployed or crimped scaffold. TABLES 1 and 2, below, provide statistics for a retention force of a polymer scaffold-balloon as a function of the scaffold temperature during crimping. The crimping process was similar to that described in FIG. 1. Two studies were conducted, one for scaffold temperatures of 37-48° C. and the other for scaffold temperatures of 48-80° C., respectively. Both tests evaluated the retention force for a PLLA scaffolding having the pattern described in US 2010/0004735 and crimped to a PEBAX balloon. More specifically, a first study included conducting several trials at each of 37° C., 42.5° C. and 48° C. and a second study included conducting several trials at each of 48° C., 55° C., 65° C. and 80° C.

TABLES 1 and 2 show the mean and standard deviation in retention force (obtained using a standard pull-off test procedure) for an 18 mm PLLA scaffolding having the pattern described in US 2010/0004735 and crimped to a PEBAX balloon. "Number" refers to the number of trials run at the corresponding scaffold temperatures.

TABLE 1

| Temp (Celsius) | Number | Mean | Std Dev |
|---|---|---|---|
| 48 | 11 | 1.18 | 0.33 |
| 55 | 9 | 1.16 | 0.15 |
| 65 | 8 | 1.41 | 0.17 |
| 80 | 4 | 2.03 | 0.20 |

TABLE 2

| Temp (Celsius) | Number | Mean | Std Dev |
|---|---|---|---|
| 37 | 20 | 0.74 | 0.19 |
| 42.5 | 21 | 1.24 | 0.11 |
| 48 | 13 | 1.24 | 0.14 |

Modifying the pressure and hold time of the scaffolding on the stent for crimping temperatures of 40° and 55° C. improved the scaffold retention. However, modifying these parameters outside of this range produce little change. Specifically, for a 40° and 55° C. range of crimping the retention may be improved by balloon pressure being increased to raise the balloon diameter to the pre-crimp stent diameter, then the stent was crimped on the balloon to a final crimp diameter while pressure is released. Additionally, the stent may be crimped down to an intermediate diameter, then the balloon is deflated then re-inflated, followed by crimping the stent down to a final crimp diameter.

Figure 2:
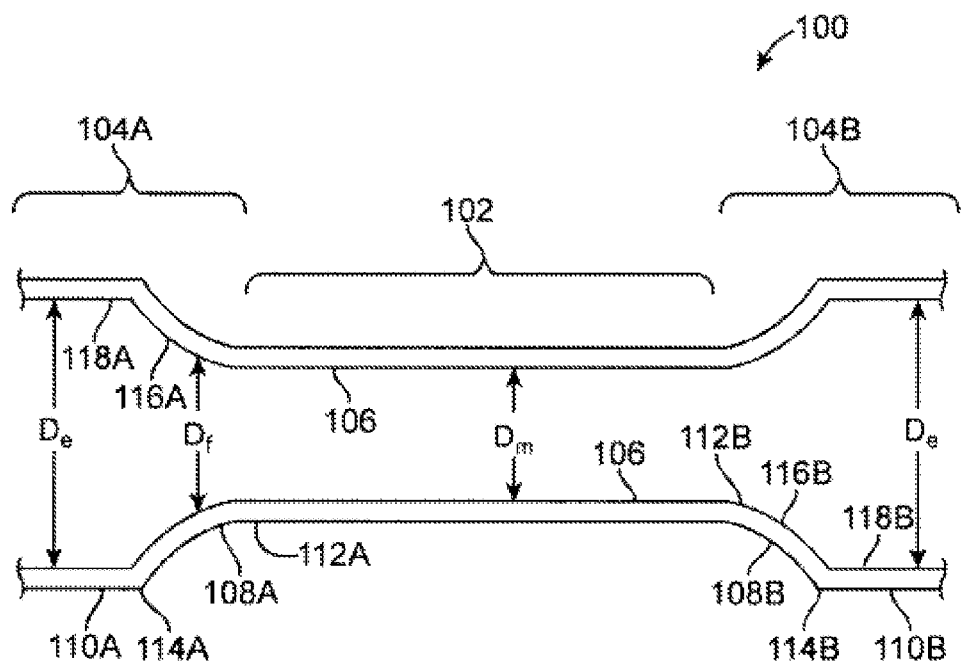
FIG. 2 depicts an axial cross-section of a flared restraining sheath.

FIG. 1 is a process diagram illustrating the steps used to fabricate a polymer scaffold and crimp the scaffold to a balloon. In this example, a scaffold was formed from a radially expanded tube of PLLA. The scaffold had a strut pattern as shown in FIG. 2. The struts had a thickness of about 0.152 mm and the balloon used was a PEBAX balloon. An iris crimper was used to crimp the scaffold to the balloon.

A crimping process may proceed as follows. In preparation for the crimping operation, the crimp head diameter is moved to an intermediate position that is larger than the scaffold starting outer diameter (OD). The temperature of the jaws is raised to, or to about 48° C. and is allowed to stabilize at that temperature. A delivery catheter (holding the balloon) is chosen with the correct size to fit the scaffold.

The scaffold is placed onto the balloon catheter with the distal portion of the scaffold aligned with the distal portion of the catheter. The catheter is then placed onto a sliding alignment carriage. A final adjustment is made to the scaffold to position it between balloon markers on the catheter. The scaffold and catheter is moved into the crimp jaws, by sliding the carrier forward.

The cycle is initiated by the operator. As an example, for a 3.0×18 mm scaffold, the ID of the crimp head moves to a diameter of 0.083" where it remains for 30 seconds. This is stage 1. The system moves automatically to stage 2 where the head moves to an ID of 0.068" and is held for 15 seconds. During this stage, the balloon catheter is inflated to 17 psi. After this stage is complete, the balloon is deflated and the crimp head is opened to allow the catheter to be removed. The scaffold receives a final alignment to the balloon markers. The scaffold and balloon are placed back into the crimp head. The operator initiates stage 3 where the head is reduced to 0.070" diameter for 10 seconds. During this stage 3, the balloon is also inflated to 17 psi. Once complete, the machine moves automatically to the stage 4, where the balloon is deflated and the crimp head ID is reduced to 0.047" and is held for 200 seconds. When this fourth and final stage is complete, the head opens and the catheter and scaffold removed. The scaffold is retained on the balloon and is immediately placed into a sheath, to prevent recoil of the scaffold.

The above study was conducted for PLLA. Similar results are contemplated for PLGA, if Tg for the different material is taken into consideration and assuming other characteristics of the process and scaffold pattern. For PLGA having % GA of about 5% the temperature ranges for crimping may be between about 46 to 53 degrees Celsius. For PLGA having % GA of about 15% the temperature ranges for crimping are about 43 to 50 degrees Celsius.

Based on the foregoing results, the following conclusions were reached. When the scaffold is crimped to a balloon while being heated to temperatures well within the range of Tg for the scaffold polymer, there is a greater tendency for polymer chain re-alignment to occur that will result in loss of strength when the scaffold is later deployed. Unacceptable crack formation (either in the number or extent of cracks), voids or outright fracture was observed in subsequent testing. It should be noted that acceptable scaffolds have cracks. The degree of crack formation that causes a scaffold to be rejected is based on tests conducted on the scaffold when fully deployed, e.g., accelerated aging, fatigue, cyclic loading and static load tests and including a visual inspection of the scaffold.

It should be noted, therefore, that some degree of crack or void formation is permissible and indeed expected. Validation of a crimping process, therefore, generally cannot be made by simply inspecting or counting the number of cracks or voids. Testing is needed to establish, to a reasonable degree of confidence, a relationship between the locations and nature of the imperfections at those locations in the scaffold and its ability to function properly. Mechanical testing is needed to assess the degree of structural integrity in the deployed polymer scaffolding. Then, relying on statistics a determination may be made as to the type, number and/or location of cracks/voids that distinguish between an acceptable and unacceptable scaffold. A scaffold, despite the presence of one or more cracks and/or voids, may then be deemed capable of being plastically expanded within a body lumen by the balloon to which it is crimped. As such, the scaffold is deemed capable of providing a therapeutic benefit to the body lumen including radially supporting the lumen despite the presence of one or more cracks/voids.

If the crimping temperature is raised too high relative to the Tg of the polymer, the memory of the matrix material at the starting tubing diameter is being removed, or reformed as the scaffold is deformed. As a consequence, when the scaffold is later expanded under physiological conditions, e.g., body temperature, it becomes more susceptible to crack formation due to its brittle properties at body temperatures and lack of chain alignment from its starting diameter. Retention force and scaffold integrity when crimped to the balloon generally improves at higher temperatures, however, the scaffold loses its structural integrity when later deployed if the temperature is raised too high relative to Tg. On the other hand, when the scaffold is heated to temperatures below about 15 degrees Celsius of the glass transition temperature, or not heated at all, there is no noticeable improvement in scaffold retention. And if the crimping force is increased to improve scaffold retention at these temperatures, loss in strength occurs as cracks appear in the crimped and deployed scaffold. It was concluded, therefore, that for a temperature below about 15 degrees from Tg the scaffold exhibited more or less the same degree of fracture toughness it would exhibit under physiological conditions.

Surprisingly, when the temperature range was raised to within a range of about 15 degrees below and up to about Tg there was a noticeable and consistent improvement in scaffold retention force, without unacceptable loss in structural integrity for the deployed scaffold. It is believed that when the polymer scaffold was crimped at a temperature slightly below its Tg (e.g., from 5 to 15 degrees Celsius below Tg), there are very short chains of the matrix material that are able to freely move to assist in the deformation of the scaffold without exceeding material stress limits. At the same time, the longer chains of the matrix substantially maintain their alignment, and, thus, stay intact without losing their orientation set when the starting tube was expanded. By doing so, the scaffold may be crimped down to a diameter for good scaffold retention, while the orientation of a majority of polymer chains would be the same to ensure desirable strength and fracture toughness in the final product, i.e., when the stent is deployed to support a vessel.

The improved scaffold retention of the approach of Jow et al. may also be explained in terms of the balloon-scaffold interaction. As noted above, when the temperature was raised to within the range of Tg, there was improved scaffold retention ability. When the temperature was below about 15 degrees Celsius of Tg there was no improvement (same crimping force used in both cases). In the former case, it is believed that with the increased temperature there is greater cohesion or contact between the scaffold and balloon resulting from the increased temperature. As the scaffold and balloon material temperatures increase, the material becomes more compliant resulting in stronger adherence between the two surfaces, or greater surface-to-surface contact especially arising from penetration of balloon material into gaps between struts. As a result, the retention force increases. For the tests, a PEBAX balloon was used.

The improved scaffold retention may also be attributed to penetration of the balloon into the gaps between the struts and beyond the outer surface of the stent. The crimping head is withdrawn from the stent which may allow balloon material to expand beyond the outer diameter of the stent. After depressurizing the balloon, the balloon material may remain beyond the outer surface of the stent and be on the surface of the stent, resulting in improved stent retention. In contrast, the method of Chiu et al. adapted for polymeric stents employs an expansion restraint that prevents balloon material from penetrating beyond the outer diameter of the stent.

Additionally, the improved stent retention of the approach of Jow et al. over the adapted method of Chiu et al. may be due to a greater amount of balloon material that penetrates into the gaps between struts. In contrast to the adapted method of Chiu et al., the penetration of balloon material occurs at a diameter greater than the crimped diameter. Since the gaps are larger at larger diameters, a greater amount of stent material penetrates into the gaps. For example, exemplary stent pattern 700 illustrated in FIGS. 7 and 8 has gaps 703. As indicated below, gaps 703 decrease in size as the diameter of the stent is reduced. When the stent is crimped to the final crimped diameter, this greater amount of material in the gaps provides a tighter fit than less material and thus increases retention. Final crimped diameter may refer to a stent crimped over a balloon that is completely depressurized or deflated.

Studies of shorter stents (e.g., 12 mm) using the Jow et al. approach show an increased likelihood of dislodgement as compared to longer stents. Table 3 shows the results of dislodgement force measurements for two sets of sample scaffoldings for two different lengths. The average dislodgement force for the 18 mm samples, 0.73 lb., was less than for the 28 mm samples, 1.14 lb. The total retention force is expected to depend on the length of the stent since the total retention force arises from the cumulative force provided by balloon-surface interaction along the length of the stent. The shorter a stent is, the lower is the total retention force provided by interference of balloon material with struts. Although it is not known whether the total dislodgement force is dependent on stent length, the inventors have found that the degree stent retention does depend on stent length for a polymeric stent.

TABLE 3

Dislodgement force measurements of PLLA scaffoldings of two lengths.

| | Dislogement force ($lb_f$) | |
|---|---|---|
| | 3.0 × 18 mm | 3.0 × 28 mm |
| Min | 0.53 | 0.80 |
| Max | 0.99 | 1.57 |
| Avg | 0.73 | 1.14 |
| Stdev | 0.13 | 0.23 |

Additionally, the stent retention force is a combination of (1) balloon surface interactions along the length of the stent and (2) interaction of the balloon beyond the ends of the stent with the end of the stent. Thus, the shorter a stent is, the greater is the contribution to the total retention force from (2). As indicated above, the Jow et al. approach focuses on improvement of stent retention through the interaction of the stent surface with the balloon and stent ends with the balloon. Therefore, the decrease in retention for shorter stents may be more pronounced as stent length decreases.

In the Jaw et al. approach, the balloon material near the ends of the stent does expand outward to conform to stent geometry at the ends when the balloon is pressurized during the crimping process. Additionally, in comparison to the method of Chiu et al, a greater amount of balloon material expands outward and against the ends of the stent since the diameter of the balloon is greater than the crimped diameter when the balloon is inflated. The struts at the end of the stent typically present a sinusoidal profile to the balloon, as illustrated by end ring 740 in FIG. 8. The angles of the struts in this sinusoidal profile are larger at stent diameters than the crimped diameter which allows for greater contact of the greater amount of balloon material against the strut ends. Therefore, a greater amount of balloon material is expected to be expanded at the ends of the stent in the Jow et al. approach as compared to Chiu et al. and other methods that involve pressurizing the balloon only when the stent is at the crimped diameter.

However, in the Jow et al. approach, the crimping head presses down the expanded balloon material at the ends when the stent is crimped to the final crimped diameter. The pressing down of the stent material reduces the retention force contribution of the balloon-stent interaction at the ends of the stent. The effect of the pressing down of balloon material is expected to be less between the ends of the stent since the balloon material may tightly wedge in between the stent struts and may be difficult to be pressed back to the inner surface of the stent.

Embodiments of the present invention include methods of making a stent-balloon assembly which provides for improved stent retention for a polymeric stent. The embodiments include steps that can be used to improve the stent retention of any polymer stent-balloon assembly in which the polymeric stent is crimped at or near the final crimp or delivery diameter of the stent. These steps include methods of improving the retention force contribution at the ends of the stent. The retention force is increased by expanding and/or stretching the portion at or beyond the ends of the stent. The expanding and/or stretching increases the contact of the balloon with the ends of the stent.

Such steps are particularly useful in improving stent retention of stent-balloon assemblies made by the Jow et al. approach. Additionally, such steps are particularly useful for improving stent retention of shorter stents, for example, those having lengths of 12 mm or less.

The various embodiments of the method include providing a stent-balloon assembly with the stent crimped over the balloon. An expansion restraint is disposed over the crimped stent. The expansion restraint prevents expansion of the stent when the balloon is pressurized. The expansion restraint may be a tubular sheath having a portion with an inner diameter equal or approximately equal to the outer diameter of the crimped stent. This portion is disposed over the stent and prevents the expansion of the stent when the balloon is pressurized.

In certain embodiments, the restraining sheath disposed over the stent includes a middle portion with a diameter equal or approximately equal to the diameter of the crimped stent. "Approximately equal" can refer up to 1% or 1-2% larger than the diameter of the crimped stent. The middle portion may have a constant diameter along its entire length. The sheath further includes end portions at each end of the sheath with an inside diameter greater than the crimped stent diameter. The end portions can have a diameter up to 3% or 3 to 100% greater than the diameter of the crimped scaffolding. The diameter of the sheath increases to greater than the crimped stent diameter at the ends of the sheath. In these embodiments, the middle portion or the restraining sheath is over the stent from its proximal to its distal end and the end portions of the sheath are over the balloon beyond the ends of the stent. For example, the proximal end portion of the sheath extends proximally from the proximal end of the middle portion over a proximal portion of the balloon.

Similarly, the distal end portion of the sheath extends distally from the distal end of the middle portion over a distal portion of the balloon.

The restraining sheath may be disposed over the crimped stent-catheter assembly using various methods. Since the inner surface of the sheath is in contact with the stent, there is a tight fit over of the sheath over the stent. The sheath should be disposed over the stent in a manner that minimizes frictional interaction with the stent surface to avoid damage to the stent or balloon and to avoid pushing the stent off the balloon. In exemplary embodiments, the sheath may be split along its axis. Each half may be secured over the stent-balloon assembly and then the halves secured in some fashion, such as with a ring over the sheath.

In these embodiments, the balloon is pressurized which causes the ends of the balloon beyond the ends of the stent to expand and/or stretch. As indicated, expansion of the stent is prevented by the middle portion of the restraining sheath. The ends of the balloon beyond the stent ends can be expanded to a diameter greater than the outer diameter of the stent. The expansion of the balloon is limited by the inner surface of the end portions of the restraining sheath. Thus, the maximum expanded balloon diameter is the maximum diameter of the end portions. The expansion causes the balloon at the ends of the stent to abut against struts, in particular the sidewalls, at the ends of the stent.

The pressure may be maintained for any selected period of time, for example, 5 to 30 sec, 10 to 30 sec, 20 to 30 sec, 20 to 60 sec, or 30 to 60 sec. The balloon may then be depressurized, causing the balloon at the ends to deflate. However, balloon at the ends remains partially raised or "puffed out" due to a pillowing effect caused by the expansion. Thus, the balloon ends that were pressed down by crimping in a stent-catheter assembly made according to Jow et al. will be raised up. The balloon also is at least partially or completely abutted against the sidewalls the end struts. The balloon diameter at the ends is thus increased by the pressurizing and depressurizing process. The balloon diameter after depressurizing may be between the inner diameter and the outer diameter of the crimped stent or may be greater than the outer diameter of the crimped stent. As a result of the above modifications of the balloon beyond the ends of the stent, the retention force is increased. This is due to an increase in the contribution of retention force attributed to the stent-balloon interaction at the ends of the stent. The restraining sheath may be kept on the stent and then removed prior to delivery into a patient. Alternatively, the sheath can be removed after depressurizing.

The geometry or structure of the end portions can take on a variety of forms. In some embodiments, the restraining sheath has flared ends that flare outward from the end of the middle portion. In one embodiment, the diameter increases or flares outward form the end of the middle portion and then becomes constant. FIG. 2 depicts an axial cross-section of a flared restraining sheath 100. Sheath 100 has a middle portion 102, a proximal end portion 104A, and a distal end portion 104B. Middle portion 102 has a constant inner diameter Dm and an inner surface 106. Proximal end portion 104A has a flared portion 108A and a constant diameter portion 110A. Flared portion 108A has a diameter Df that varies (increases) from the end 112A of middle portion 102 to De at the end 114A of flared portion 108A. Constant diameter portion 110A has the diameter De. Flared portion 108A has an inner surface 116A and constant diameter portion 110A has an inner surface 118A. The various corresponding features of the distal end portion 104B are labeled, but not described. The invention includes various minor variations of the restraining sheath as described, including that the specific dimensions of the two end portions need not be identical.

Figure 3:
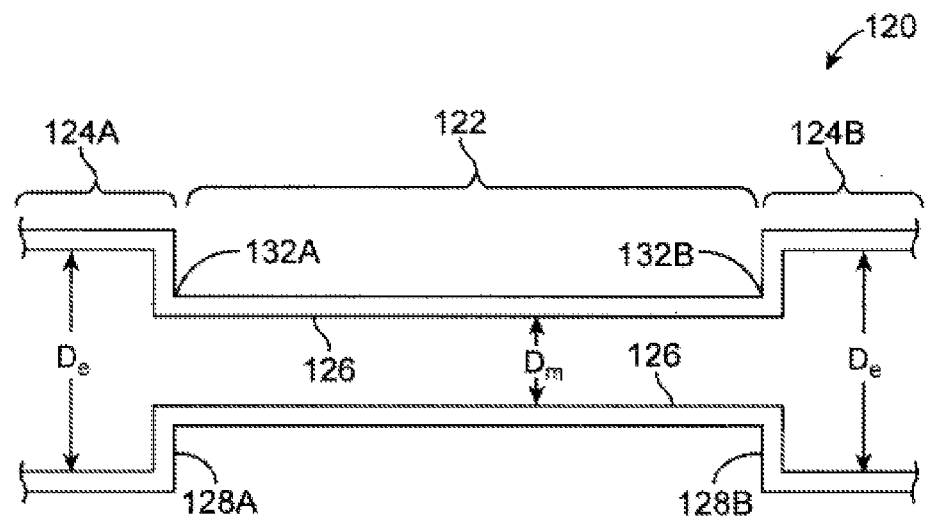
FIG. 3 depicts an exemplary restraining sheath with a step-change in diameter between a middle portion and end portions.

In other embodiments, the diameter of an end portion of a restraining sheath can be constant along its entire length. In such a structure, the diameter of the sheath can increase abruptly or with a step-change at the ends of the middle portion to a selected diameter. FIG. 3 depicts an exemplary restraining sheath 120 with a step-change in diameter between a middle portion 122 and end portions. Sheath 120 has middle portion 122 between a proximal end portion 124A and a distal end portion 124B. Middle portion 122 has a constant diameter Dm and an inner surface 126. Proximal end portion 124A has a step-change 128A at the end 132A of middle portion 122 from Dm to De. The various features of the distal end portion 124B are labeled, but not described. The invention includes various minor variations of the restraining sheath as described, including that the specific dimensions of the two end portions need not be identical.

Figure 4:
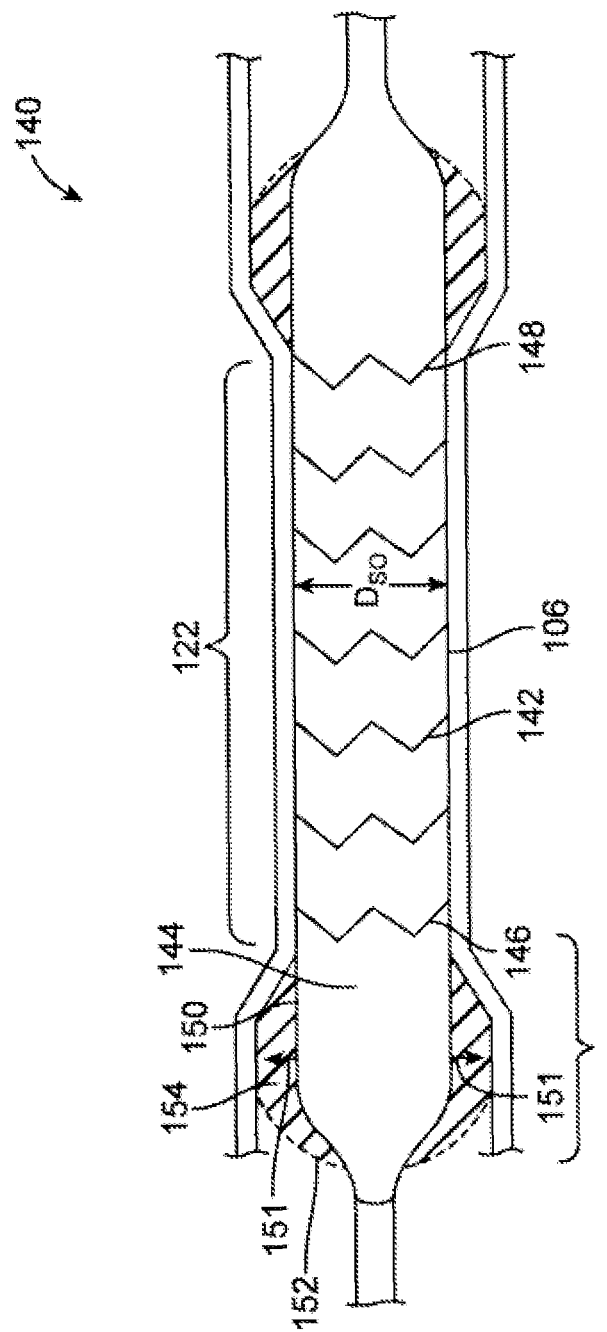
FIG. 4 illustrates a method of expanding balloon ends of a crimped stent-balloon assembly using the restraining sheath of FIG. 2.

FIG. 4 illustrates expanding balloon ends of a crimped stent-balloon assembly using the restraining sheath of FIG. 2. FIG. 4 shows sheath 100 disposed over a crimped stent-balloon assembly. Stent 142 is crimped over balloon 144. Middle portion 122 of sheath 100 is disposed over stent 142 from proximal end 146 to distal end 148 of stent 142. Stent 142 outer diameter, Dso, is equal to the inner diameter Dm of middle portion 122 so that the outer surface of stent 142 contacts the inner surface 106 of middle portion 102. The detail of the stent struts showing their thickness is neglected for the sake of clarity of explaining the method. Struts are shown in detail in an expanded view of FIG. 4 in FIG. 5.

The description of the method will focus on the proximal end of the stent-balloon assembly and sheath, however, it is understood that the description for the distal end is the same or similar. Proximal end portion 104A is over the portion of balloon 144 that extends proximally beyond stent proximal end 146. Surface 150 of balloon 144 is shown prior to pressurizing the balloon. When balloon 144 is pressurized the portion of balloon 144 beyond stent proximal end 146 expands and/or stretches in the direction of arrows 151 as shown by surface 152 of balloon 144 after pressurizing. The shaded region 154 illustrates the expanded proximal end of balloon 144. Balloon 144 is shown to expand against the inner surface of proximal end portion 104A of sheath 100.

Figure 5:
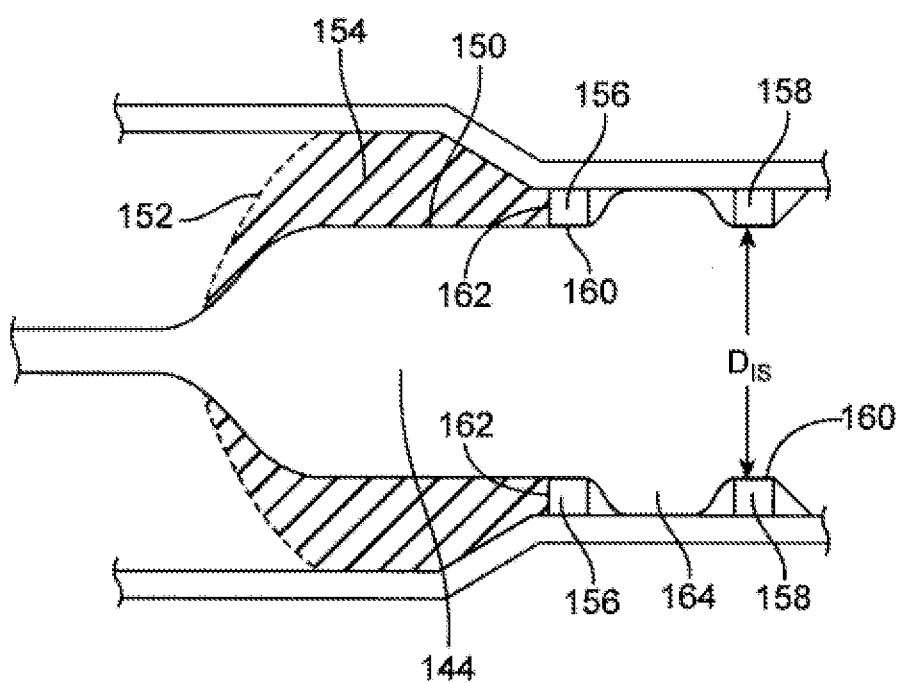
FIG. 5 depicts an expanded view of the proximal end of a restraining sheath disposed over a stent-balloon assembly of FIG. 4.

FIG. 5 depicts an expanded view of the proximal end of sheath 100 disposed over the stent-balloon assembly from FIG. 4. FIG. 5 shows proximal end struts 156 and struts 158 between the proximal and distal end of the strut. Stent 142 has an inner diameter D is between opposing inner surfaces 160 of radially opposed struts. Surface 150 of balloon 144 is shown to abut against inner surfaces 160 of stent 142, both before and after expansion. Prior to expansion, balloon surface 150 also penetrates into gaps 164 between adjacent struts, making contact with the sidewalls of the struts. However, prior to pressurizing, surface 150 of balloon 144 may have, some, little, or no contact with sidewalls 162 of proximal end struts 156. After pressurizing the balloon 144, balloon 144 abuts against sidewalls 162 of proximal end struts 156.

Figure 6:
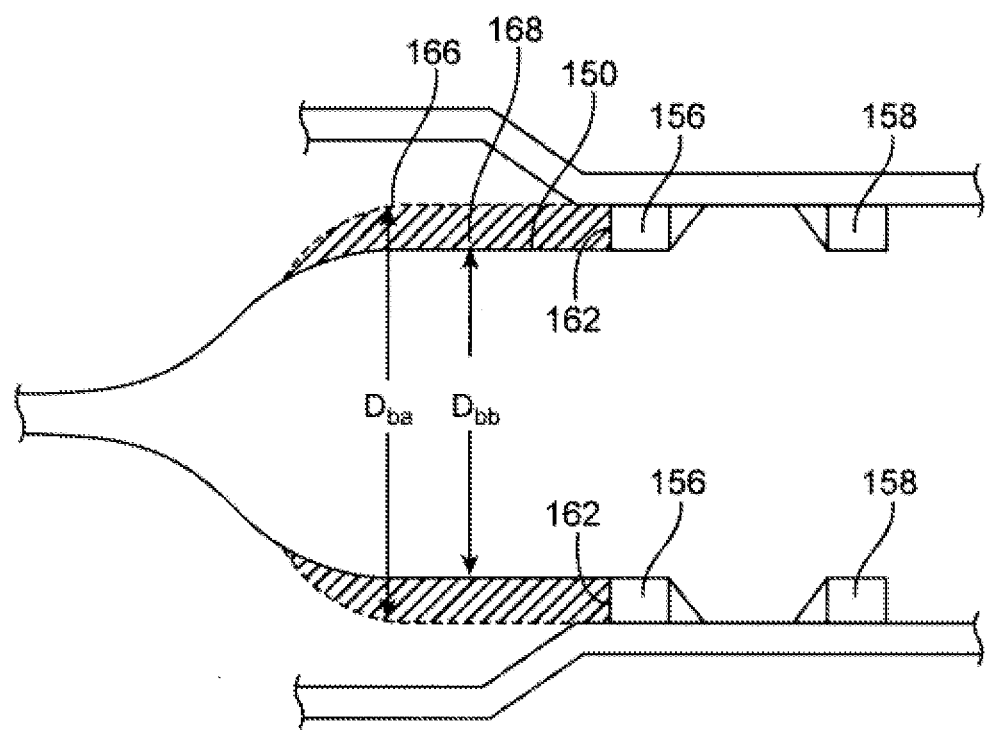
FIG. 6 depicts the expanded view of FIG. 5 after the balloon is depressurized.

FIG. 6 depicts the expanded view of FIG. 5, after balloon 144 is depressurized. Surface 166 of balloon 144 is depicted in FIG. 6 and the shaded region represents the degree of balloon expansion or pillowing provided by the pressurizing/depressurizing process. The diameter Dba of the balloon ends after the process is greater than the diameter of the balloon ends before the process (Dbb). As shown, balloon 144 is abutted against sidewalls 162 of end struts 156.

An exemplary embodiment of the pressurizing/depressurizing process of the present invention includes disposing a scaffold crimped or retained on a balloon such as that from Jow et al., for example, after stage 4 described above. The sheath is as illustrated in FIG. 4. The inner diameter of the sheath over the stent is 0.047". The diameter De of the end portion of the sheath is 0.078". The balloon is pressurized to a pressure of 100 psi which expands the balloon end portions to the inner surface of the end portions. The pressure is held for 60 secs. The balloon is depressurized. The stent is retained in the sheath until delivery.

Embodiments of the present invention may provide a retention force of between 0.7 to 3 lb. Embodiments of the present invention may provide a retention force of between 0.7 to 3 lb. for a stent having a length of less than 12 mm, more narrowly, less than 5 mm, 5 to 12 mm, 8 to 12 mm, 10 to 15 mm, 12 to 18 mm, or greater than 18 mm.

The embodiments of the pressurizing and depressurizing of the end portions of the crimped stent/balloon assembly is a significant improvement over previous methods of stent retention. The method improves upon the Jow et al. approach since balloon material at the ends that is pushed down by a final crimp to the crimped diameter is raised back up by the process. The contribution to the retention force due to stent ends may be increased significantly which is important for any stent, but is very important for shorter stents since the end contribution to retention force represents a larger percentage of the total retention force.

Also, the present method of expanding balloon ends selectively of a stent-catheter assembly to a diameter greater than the stent outer diameter is an advantage over methods that limit expansion of the balloon to the stent outer diameter, such as Chiu et al. Such a method enhances the pillowing effect of the balloon at the ends and provides better stent-balloon interaction to improve stent retention. The balloon at the ends may be in contact with the outer surface of the stent which further increases stent retention.

Additionally, the embodiments of expanding the balloon ends in combination with the method of Jow et al. which provides a crimped stent-balloon catheter assembly are an improvement over an approach involving pressurizing the balloon only after the stent is crimped to a final crimped delivery diameter over a deflated delivery balloon. As explained above, pressurizing the balloon at a diameter greater than the final crimped diameter, as done in Jow et al., provides a greater amount of balloon material expanded outward or puffed out at the ends of the stent. When the balloon is pressurized at the crimped stent diameter according to the methods of the present invention, there is more balloon material to puff outward resulting in better stent retention.

In further embodiments, a method can include crimping according to a method that includes at least one crimping step in which the stent is crimped to a first diameter greater than the final diameter and holding the scaffolding at the first diameter while the balloon is inflated to a pressure against the scaffolding, such as in the method of Jaw et al. The crimped stent is then disposed on a restraining sheath over the crimped stent that has a constant diameter that extends along the length of the stent and beyond the proximal and distal ends of the stent. Thus, referring to the embodiments above, the middle portion has the same diameter as the end portions. The fit of the sheath over the stent is as described above. In some embodiments, the end portions can have a diameter slightly less than the diameter of the middle portion. The balloon is pressurized, as described herein, which causes the ends of the balloon beyond the ends of the stent to expand and/or stretch. The ends of the balloon beyond the stent ends can be expanded to the inner diameter of the sheath. The expansion causes the balloon at the ends of the stent to abut against strut sidewalls at the ends of the stent. This method is superior to the method of Chiu et al. (which involves pressurizing the balloon only after the stent is crimped to a final crimped delivery diameter) since a stent crimped with an inflation step, as indicated above, has more balloon material to puff outward against the ends of stent when the balloon is pressurized. The balloon is then depressurized.

It is expected that the degree of expansion of the balloon ends will influence the degree of abutment of balloon ends on the end struts and the degree of pillowing after the pressurizing/depressurizing of the balloon ends. The radial distance, Le, is defined as ½ (Dexp−Dm) is the radial expansion of the balloon beyond the inner surface of the struts and ts is the strut thickness. Le may be 1-1.5, 1.5-2, 2-2.5, 2-3, 3-4, 4-6, 6-8, 8-10, 10-15, 15-20, or 20-30 times ts. The selected Le may be used to determine Dexp and the De (diameter of the end portion) may be set to Dexp to limit expansion to Dexp.

In further embodiments, the restraining sheath has no end portions. The restraining sheath is disposed over the stent and does not extend proximally or distally beyond the proximal or distal end of the stent, respectively. Therefore, when the ends of the balloon expand, the balloon end expansion is not limited by a restraining surface. However, the advantage of the sheath beyond the stent ends is that it controls the expansion and prevents over expansion and stretching that could damage the balloon or prevent the balloon from returning to the "folded" shape after being depressurized. Additionally, the controlled expansion outward allows for better contact of the balloon with the end struts.

Figure 7:
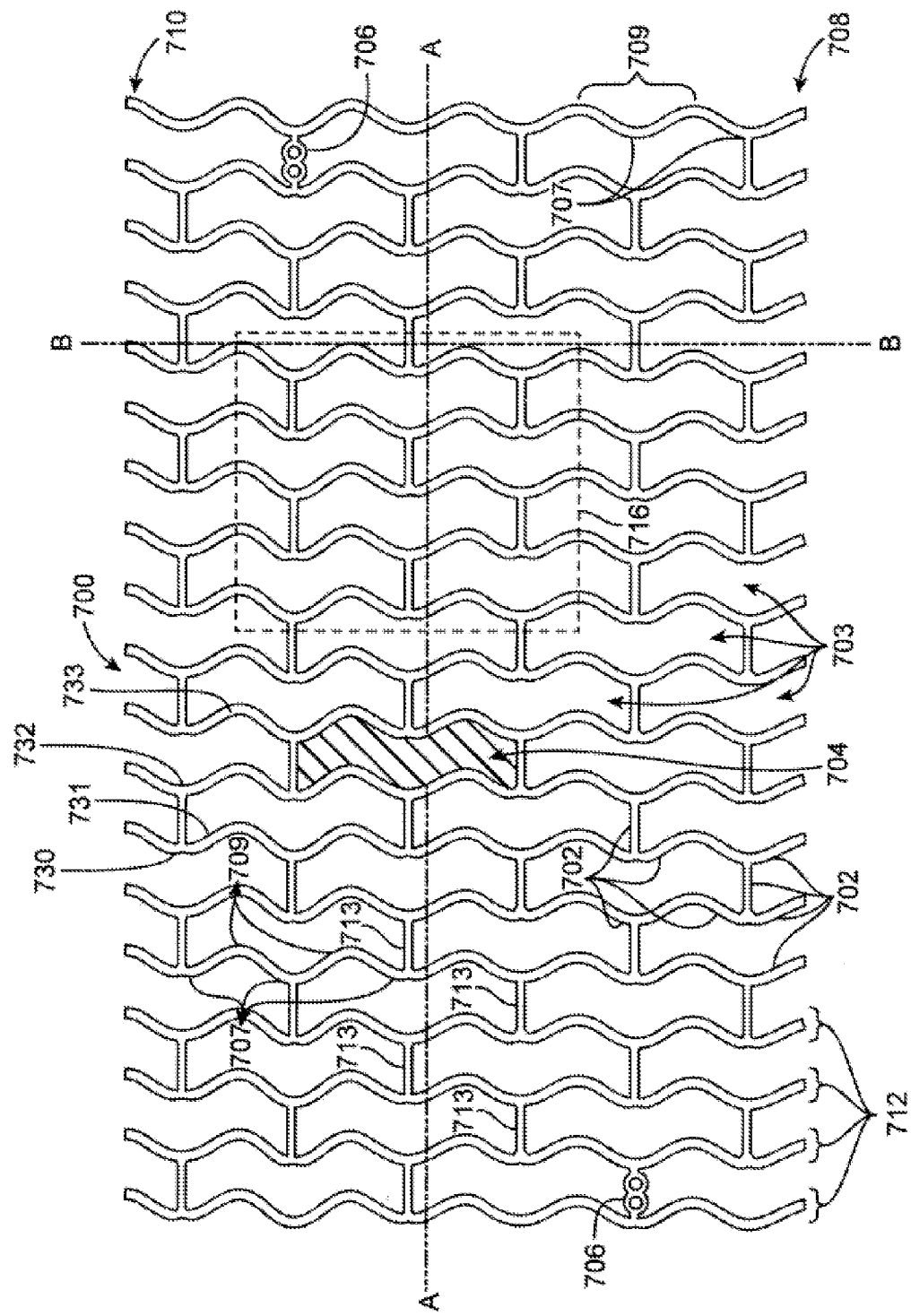
FIG. 7 depicts and exemplary stent pattern 700 from US 2008/0275537.

In a preferred embodiment a stent scaffold has the stent pattern described in U.S. application Ser. No. 12/447,758 (US 2010/0004735) to Yang & Jow, et al. Other examples of stent patterns suitable for PLLA are found in US 2008/0275537. FIG. 7 depicts exemplary stent pattern 700 from US 2008/0275537. The stent pattern 700 is shown in a planar or flattened view for ease of illustration and clarity, although the stent pattern 700 on a stent actually extends around the stent so that line A-A is parallel or substantially parallel to the central axis of the stent. The pattern 700 is illustrated with a bottom edge 708 and a top edge 710. On a stent, the bottom edge 708 meets the top edge 710 so that line B-B forms a circle around the stent. In this way, the stent pattern 700 forms sinusoidal hoops or rings 712 that include a group of struts arranged circumferentially. The rings 712 include a series of crests 707 and troughs 709 that alternate with each other. The sinusoidal variation of the rings 712 occurs primarily in the axial direction, not in the radial direction. That is, all points on the outer surface of each ring 712 are at the same or substantially the same radial distance away from the central axis of the stent.

The stent pattern 700 includes various struts 702 oriented in different directions and gaps 703 between the struts. Each gap 703 and the struts 702 immediately surrounding the gap 703 define a closed cell 704. At the proximal and distal ends of the stent, a strut 706 includes depressions, blind holes, or through holes adapted to hold a radiopaque marker that allows the position of the stent inside of a patient to be determined.

One of the cells 704 is shown with cross-hatch lines to illustrate the shape and size of the cells. In the illustrated embodiment, all the cells 704 have the same size and shape. In other embodiments, the cells 704 may vary in shape and size.

Still referring to FIG. 7, the rings 712 are connected to each other by another group of struts that have individual lengthwise axes 713 parallel or substantially parallel to line A-A. The rings 712 are capable of being collapsed to a smaller diameter during crimping and expanded to their original diameter or to a larger diameter during deployment in a vessel. Specifically, pattern 700 includes a plurality of hinge elements 731, 732, 733, 734. When the diameter of a stent having stent patter 700 is reduced or crimped, the angles at the hinge elements decrease which allow the diameter to decrease. The decrease in the angles results in a decrease in the surface area of the gaps 703.

Figure 8:
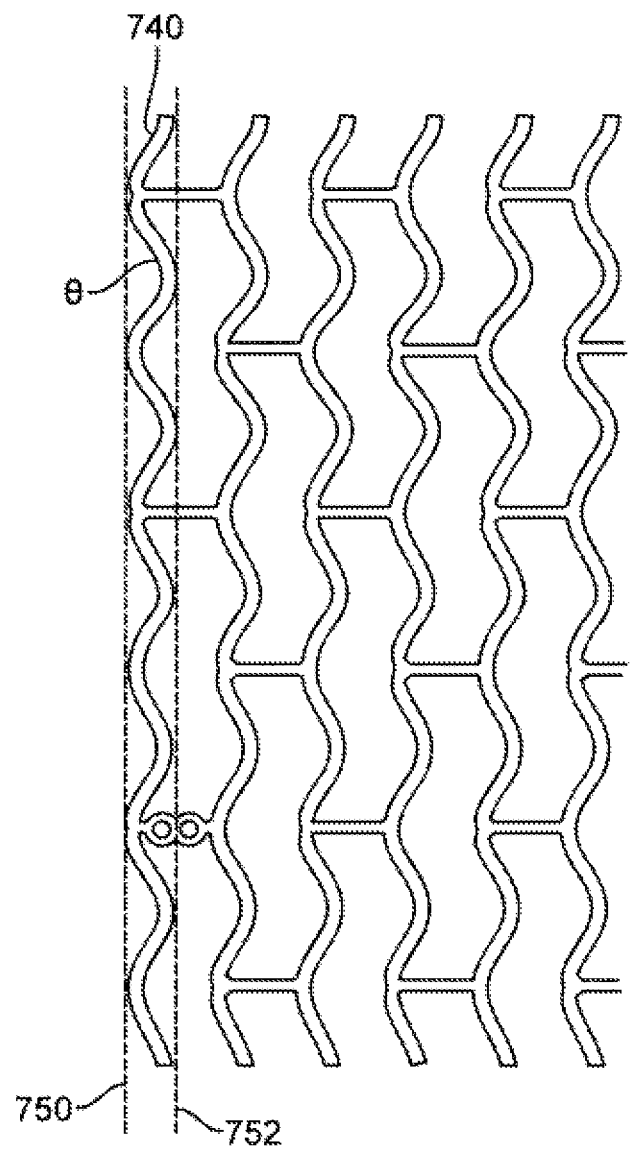
FIG. 8 depicts the proximal end portion of pattern 700 in FIG. 7.

FIG. 8 depicts the proximal end portion of pattern 700 in FIG. 7. As can be seen in FIGS. 7 and 8, the profile of the proximal end ring 740 presents a sinusoidal profile or edge. The pattern is shown in a condition that corresponds to a diameter greater than crimping, therefore, when the pattern is crimped, the angles, Θ, will be less when the stent is in a final crimped condition. The proximal edge of the middle portion of the restraining sheath may be positioned, for example, anywhere from the crests of the proximal end ring, as indicated by dashed line 750, to the troughs of the proximal end ring, as indicated by dashed line 752. The latter choice may maximize contact of the balloon ends with the sidewalls of the end ring. The proximal edge of the middle portion may also be distal or proximal to lines 750 and 752. Similarly, the distal edge of the middle portion of the restraining sheath may be positioned anywhere from the crests of the distal end ring to the troughs of the distal end ring. In other embodiments, the proximal and distal edges of the restraining sheaths have a profile, such as a sinusoidal profile that matches the profile of the end rings.

In further embodiments, the method includes providing a crimped stent-catheter assembly with the stent crimped according the Jow et al. approach described herein. A restraining sheath is disposed over the stent and the portion of the balloon beyond the ends of the stent. The sheath has a diameter which is the diameter of the crimped stent. The expansion restraint prevents expansion of the stent when the balloon is pressurized. The expansion restraint also prevents the portion of the balloon beyond the ends of the stent from expanding beyond an outer diameter of the stent.

The balloon is then pressurized which causes the ends of the balloon beyond the ends of the stent to expand and/or stretch. The maximum diameter of the expanded balloon is the inner diameter of the sheath which is outer diameter of the stent. As indicated, expansion of the stent is prevented by the restraining sheath. The expansion of the balloon is limited by the inner surface of the restraining sheath. The expansion causes the balloon at the ends of the stent to abut against the sidewalls of the struts at the ends of the stent.

The pressure may be maintained for any selected period of time, for example, 5 to 30 sec, 10 to 30 sec, 20-30 sec, 20 to 60 sec, or 30 to 60 sec. The balloon may then be depressurized, causing the balloon at the ends to deflate. However, balloon at the ends remains partially raised or "puffed out" due to a pillowing effect caused by the expansion. The balloon also is at least partially abutted against the sidewalls at the end struts. The balloon diameter at the ends is increased by the pressurizing and depressurizing process. As a result of the above modifications of the balloon beyond the ends of the stent, the retention force is increased. This is due to an increase in the contribution of retention force attributed to the ends of the stent. This embodiment of the method will provide superior retention over the Chiu et al. approach discussed above, since as indicated above the method of Jow et al. results in a greater amount of balloon material at the ends of a crimped stent since Jow et al. pressurized the balloon at a diameter greater than the crimped diameter.

Additionally, the ends of the balloon in any of the embodiments can be heated to facilitate the expansion of the balloon beyond the stent ends when pressurized. Various methods may be used to heat the balloon ends including radiant heating or blowing a warm gas with a nozzle onto the end portions of the sheath. The temperature of the stent can be controlled during the heating to reduce or eliminate potentially harmful effect of heating on the stent coating or scaffolding mechanical properties. Methods of controlling the temperature of the stent are described in Chiu et al. and may be applied to embodiments of the present invention. For example, the stent may be thermally insulated from the balloon ends beyond the ends of the stent. In exemplary embodiments, the balloon may be heated from 80° C. to 95° C.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a stent delivery system, comprising the steps of:
   fabricating a scaffolding from a tube made from a polymer having a glass transition temperature (Tg), the scaffolding having a diameter;
   providing a catheter comprising a balloon having a deployed diameter; and
   mounting the scaffolding on the balloon so as to increase a retention force between the scaffolding and the balloon, including
   while the scaffolding has a temperature of between Tg and 15 degrees below Tg,
      reducing the scaffolding diameter from a first size to a second size,
      placing the scaffolding and balloon within a sheath when the scaffolding diameter has the second size, wherein ends of the sheath are between ends of the balloon, and
      forming pillows at the balloon ends including inflating the balloon while the scaffolding and balloon are within the sheath;
   wherein the sheath is removed from the scaffolding before the scaffolding is placed within a patient.

2. The method of claim 1, wherein the sheath restrains radial expansion of the scaffolding.

3. The method of claim 2, wherein the sheath includes a central portion comprising the ends and flared portions extending beyond the ends and disposed over the balloon ends.

4. The method of claim 3, wherein the balloon ends increase in size to form the pillows having a pillow size and the sheath flared portions restrain the balloon ends to the pillow size when the balloon is inflated.

5. The method of claim 1, wherein the second size is at least 2.5 times less than the balloon's deployed diameter.

6. The method of claim 1, wherein the polymer comprises poly (L-lactide) and the temperature is between 55 Deg. Celsius and 40 Deg. Celsius.

7. The method of claim 1, wherein the tube diameter is larger than the balloon deployed diameter.

8. A method of making a stent delivery system, comprising the steps of:
fabricating a scaffolding from a tube made from a polymer having a glass transition temperature (Tg), the scaffolding having a diameter and a plurality of struts;
providing a catheter comprising a balloon having a deployed diameter;
mounting the scaffolding on the balloon so as to increase a retention force between the scaffolding and the balloon, including
reducing the scaffolding diameter from a first size to a second size, wherein the diameter is reduced from the first size to a second size using an iris crimper having crimper jaws that press a strut of the scaffolding into a surface of the balloon;
wherein the scaffolding has an elevated temperature of between Tg and 15 degrees below Tg while the crimper jaws are pressing the strut into the balloon surface;
forming pillows at the balloon ends including inflating the balloon while the scaffolding and balloon are disposed within a sheath;
wherein the sheath is removed from the scaffolding before the scaffolding is placed within a patient.

9. The method of claim 8, wherein the tube diameter is larger than the balloon deployed diameter.

10. The method of claim 8, wherein the forming pillows at the balloon ends including inflating the balloon while the scaffolding and balloon are disposed within the sheath further includes the step of:
while the scaffolding ends are thermally insulated from the balloon ends, heating the balloon ends.

11. The method of claim 8, wherein the balloon is pressurized when reducing the scaffolding diameter from the first size to the second size.

12. The method of claim 8, wherein the balloon is pressurized when reducing the scaffolding diameter to the third size.

13. The method of claim 8, wherein while reducing the scaffolding diameter to the second size or third size balloon material penetrates into gaps between stent struts.

14. A method of making a stent delivery system, comprising the steps of:
fabricating a scaffolding from a tube made from a polymer comprising poly(L-lactide), the scaffolding having a diameter and a plurality of struts;
providing a catheter comprising a balloon having a deployed diameter;
mounting the scaffolding on the balloon so as to increase a retention force between the scaffolding and the balloon, including
using a crimping device, reducing the scaffolding diameter from a first size to a second size,
removing the scaffolding and balloon from the device after the scaffolding diameter is reduced to the second size,
returning the scaffolding and balloon to the device wherein the scaffolding is aligned between balloon markers,
reducing the scaffolding diameter to a third size, less than the second size, using the device, wherein the balloon deployed diameter is at least 2.5 times more than the third size,
placing the scaffolding and balloon within a sheath, wherein ends of the sheath are between ends of the balloon, and
forming pillows at the balloon ends including inflating the balloon while the scaffolding and balloon are within the sheath;
wherein the sheath is removed from the scaffolding before the scaffolding is placed within a patient.

15. The method of claim 14, wherein the tube diameter is larger than the balloon deployed diameter.

16. The method of claim 14, wherein the forming pillows at the balloon ends including inflating the balloon while the scaffolding and balloon are within the sheath further includes the step of:
while the scaffolding ends are thermally insulated from the balloon ends, heating the balloon ends.

17. The method of claim 14, wherein the balloon is pressurized when reducing the scaffolding diameter from the first size to the second size.

18. The method of claim 14, wherein the balloon is pressurized when reducing the scaffolding diameter to the third size.

19. The method of claim 14, wherein while reducing the scaffolding diameter to the second size or third size balloon material penetrates into gaps between stent struts.

* * * * *